(12) United States Patent
Subrahmanyan et al.

(10) Patent No.: US 8,772,731 B2
(45) Date of Patent: Jul. 8, 2014

(54) APPARATUS AND METHOD FOR SYNCHRONIZING SAMPLE STAGE MOTION WITH A TIME DELAY INTEGRATION CHARGE-COUPLE DEVICE IN A SEMICONDUCTOR INSPECTION TOOL

(71) Applicant: KLA-Tencor Corporation, Milpitas, CA (US)

(72) Inventors: Pradeep Subrahmanyan, Los Altos, CA (US); Daniel Wack, Fredericksburg, VA (US); Michael Wright, San Carlos, CA (US); David Alles, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/862,148

(22) Filed: Apr. 12, 2013

(65) Prior Publication Data

US 2013/0270444 A1    Oct. 17, 2013

Related U.S. Application Data

(60) Provisional application No. 61/624,317, filed on Apr. 15, 2012.

(51) Int. Cl.
*G01J 1/42*    (2006.01)

(52) U.S. Cl.
USPC ........................................ 250/372

(58) Field of Classification Search
USPC ........................................ 250/372
See application file for complete search history.

(56) References Cited

U.S. PATENT DOCUMENTS

| | | | | |
|---|---|---|---|---|
| 5,990,952 | A * | 11/1999 | Hamasaki | 348/311 |
| 6,747,766 | B1 * | 6/2004 | Kamisuwa et al. | 358/505 |
| 2007/0058076 | A1 * | 3/2007 | Seo | 348/373 |
| 2008/0297786 | A1 * | 12/2008 | Fukushima et al. | 356/244 |
| 2008/0310938 | A1 * | 12/2008 | Inoue et al. | 414/151 |

* cited by examiner

*Primary Examiner* — Kiho Kim
(74) *Attorney, Agent, or Firm* — Simpson & Simpson, PLLC

(57) ABSTRACT

A method for synchronizing sample stage motion with a time delay integration (TDI) charge-couple device (CCD) in a semiconductor inspection tool, including: measuring a lateral position of a stage holding a sample being inspected; measuring a vertical position of the stage; determining a corrected lateral position of an imaged pixel of the sample based on the measured lateral and vertical positions; and synchronizing charge transfer of the TDI CCD with the corrected lateral position of the imaged pixel.

19 Claims, 5 Drawing Sheets

APPARATUS AND METHOD FOR SYNCHRONIZING SAMPLE STAGE MOTION WITH A TIME DELAY INTEGRATION CHARGE-COUPLE DEVICE IN A SEMICONDUCTOR INSPECTION TOOL

CROSS-REFERENCE TO RELATED APPLICATIONS

This application claims the benefit under 35 U.S.C. §119(e) of U.S. Provisional Patent Application No. 61/624,317, filed Apr. 15, 2012, which application is incorporated herein by reference.

TECHNICAL FIELD

The present disclosure relates to an apparatus and method for synchronizing sample stage motion with a time delay integration charge-couple device in a semiconductor inspection tool. In particular, the apparatus and method corrects lateral displacement due to trigonometric coupling of lateral and vertical velocities of a stage holding the sample for inspection.

BACKGROUND

FIG. 1 is a schematic block diagram of prior art system 10 of generating a pixel clock for a semiconductor inspection system. On known platforms used in the inspection of photomasks with a normally incident chief ray, there is no coupling between the lateral (X direction) and vertical (Z direction) degrees of freedom. System 10 includes interpolating encoder 12 and phase lock loop 14 with phase detector 16 and voltage controlled oscillator (VCO) 18. Divider 20 is in feedback loop 22. Frequency control and phase accumulator circuit 24 combines signal 26 with signal 28 to generate pixel clock 30 used to control a transfer of charge in a time delay integration (TDI) charge-coupled device (CCD). Loop 14 synchronizes the pixel clock signal to the "varying" lateral velocity of the imaged pixels on the stage.

In addition to varying the pixel clock frequency with stage velocity, block 32 corrects, using map 34, for non-linearities in an X direction stage servo resulting from imperfect encoders, granite maps etc. Operation of system 10 is accomplished in a two stage process. First, the output of the VCO is generated. Then, the output of the VCO clocks circuit 24, which generates the pixel or line clock.

FIG. 2 is a schematic representation of known semiconductor inspection system 100 using off-axis illumination. Because no optical materials are transparent for extreme ultra-violet EUV, off-axis illumination must be used for EUV mask inspection, for example, of a multi-layer mask. For example, EUV source 102 transmits EUV chief ray 104 to surface 106 of photo-mask 108 at angle of illumination θ. Ray 104 reflects off of surface 104 at angle θ to TDI CCD 112, which transfers charges to generate and transmit data to processor 114 for generation of pixel images of the areas of surface 106 illuminated by ray 104. Typical angles of illumination are on the order of 6 to 8 degrees.

The use of ray 104 leads to a trigonometric coupling between vertical (X direction) and lateral (Z direction) motions of stage 116 holding the photo-mask for inspection. For example, the coupling results in apparent lateral position 118 for an imaged pixel that is displaced by amount δx (lateral error motion) from actual lateral position 120 for the pixel. The Z motion can result from a number of sources such as the surface map of the photo-mask and error motions in a Z direction stage servo due to the disturbance forces. The lateral error motion is significant enough to cause significant blur in the pixel images. Thus, the coupling described above poses problems with known methods of synchronizing photo-mask stage motions to the movement of charges across a TDI CCD. For example, system 10 is unable to address or provide a solution to the lateral error motion.

SUMMARY

According to aspects illustrated herein, there is provided a method for synchronizing sample stage motion with a time delay integration (TDI) charge-couple device (CCD) in a semiconductor inspection tool, including: measuring a lateral position of a stage holding a sample being inspected; measuring a vertical position of the stage; determining a corrected lateral position of an imaged pixel of the sample based on the measured lateral and vertical positions; and synchronizing charge transfer of the TDI CCD with the corrected lateral position of the imaged pixel.

According to aspects illustrated herein, there is provided an apparatus for controlling charge transfer for a time delay integration (TDI) charge-coupled device (CCD) for a semiconductor inspection system, including: a phase and frequency controller arranged to generate a reference signal based on measured vertical and lateral positions of a stage holding a sample being inspected; and a control system arranged to generate, using the reference signal, a pixel clock to control charge transfer of the CCD for an imaged pixel of the sample in a corrected lateral position.

According to aspects illustrated herein, there is provided an apparatus for controlling charge transfer for a time delay integration (TDI) charge-coupled device (CCD) for a semiconductor inspection system, including: a phase and frequency controller arranged to generate a reference signal based on measured vertical and lateral positions of a stage holding a sample being inspected; and a control system: including a phase lock loop arranged to generate a control signal based on the reference signal; and arranged to generate, using the control signal, a pixel clock to control charge transfer of the CCD and to correct a difference between an apparent lateral position of an imaged pixel of the sample and an actual lateral position of the imaged pixel. Light used to charge the CCD is reflected from a surface of the sample at an acute angle. The reference signal generator is arranged to generate the reference signal based on the acute angle.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements of the disclosure. It is to be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure.

Figure 3:
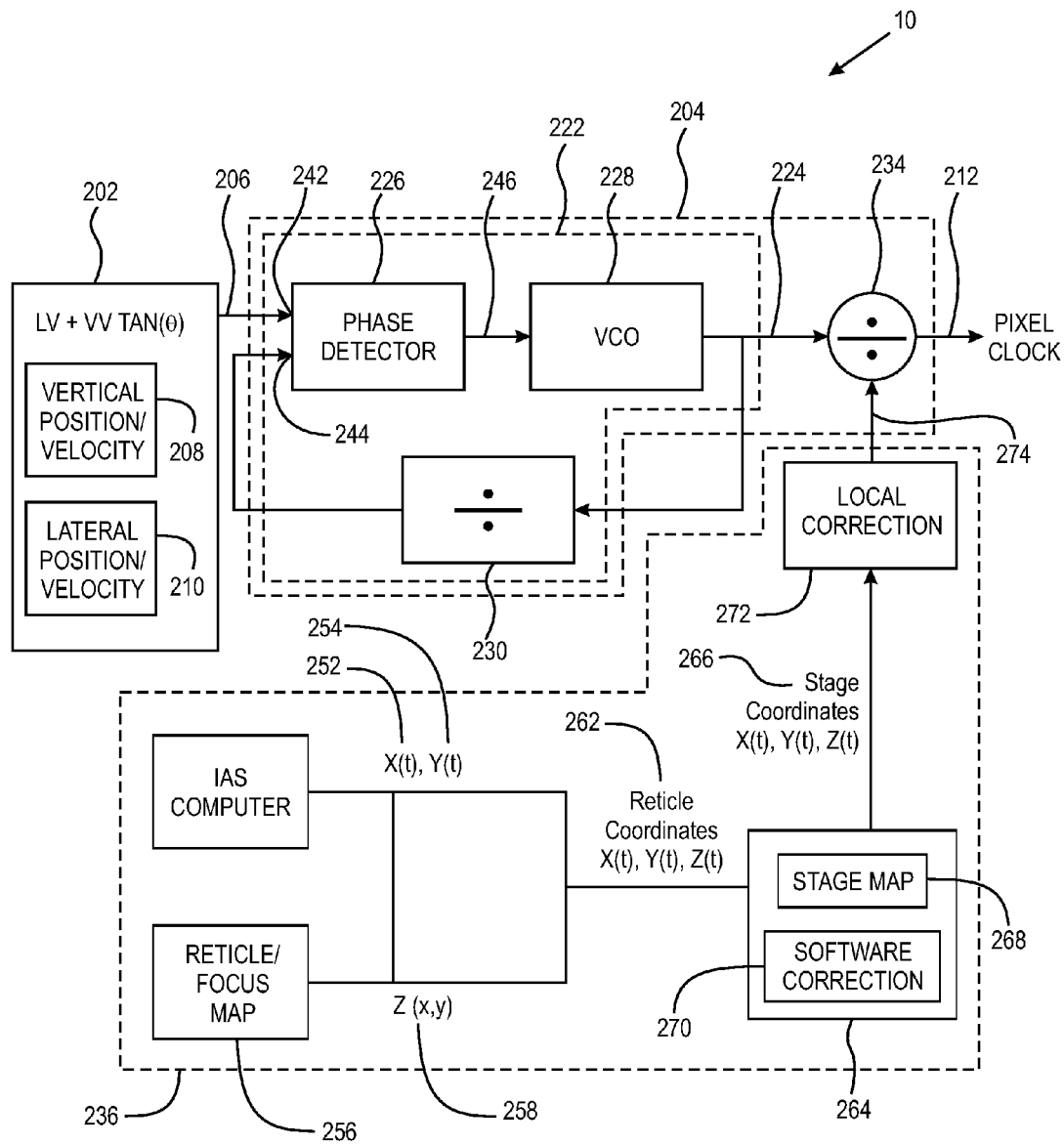
FIG. 3 is a schematic block diagram of an apparatus for synchronizing sample stage motion with a time delay integration charge-couple device in a semiconductor inspection tool.

FIG. 3 is a schematic block diagram of apparatus 200 for synchronizing sample stage motion with a time delay integration charge-couple device in a semiconductor inspection tool.

Figure 4:
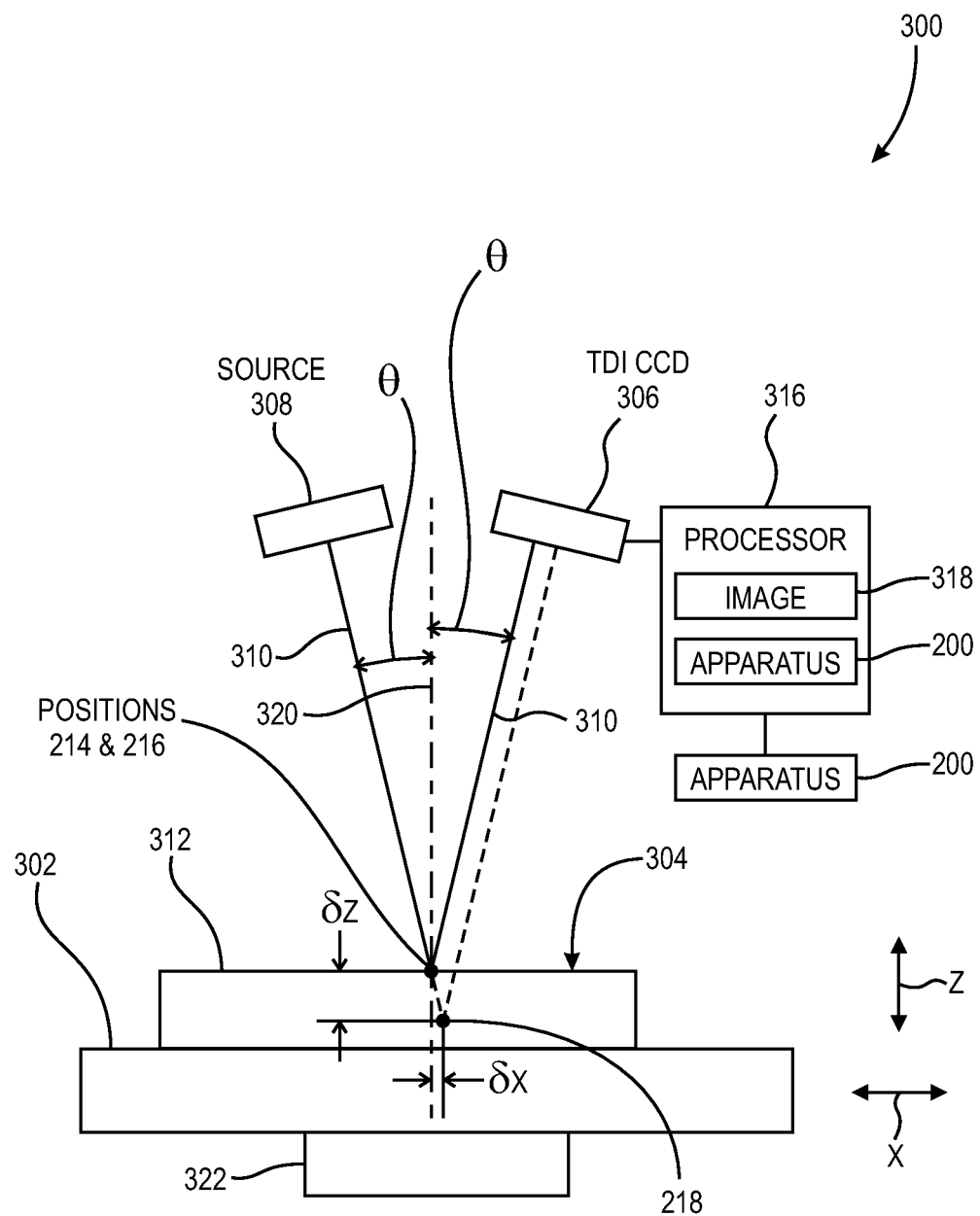
FIG. 4 is a schematic representation of a semiconductor inspection system using off-axis illumination and an apparatus and method for synchronizing sample stage motion with a time delay integration charge-couple device in a semiconductor inspection tool.

FIG. 4 is a schematic representation of a semiconductor inspection system using off-axis illumination and an apparatus and method for synchronizing sample stage motion with a time delay integration charge-couple device in a semiconductor inspection tool. The following should be viewed in light of FIGS. 3 and 4. It should be understood that only those portions of a typical semiconductor inspection system relevant to the description of apparatus 200 are illustrated. Apparatus 200 includes: phase and frequency controller 202 and control system 204. Controller 202 is arranged to generate reference signal 206 based on measured vertical position 208 and measured lateral position 210 of stage 302 holding sample 304 being inspected. Control system 204 is arranged to generate, using reference signal 206, pixel clock 212 to control charge transfer of CCD 306, for an imaged pixel of the sample in corrected lateral position 214.

As further described below: generating reference signal 206 includes modifying vertical velocity VV of the stage. As noted above, lateral velocity LV and vertical velocity VV of the stage are trigonometrically coupled. This coupling distorts actual lateral position 216 of the imaged pixel, for example resulting in apparent lateral position 218. Generating pixel clock 212 includes compensating for the distortion.

As noted above, because no optical materials are transparent for extreme ultra-violet EUV, off-axis illumination must be used for EUV mask inspection. For example, EUV source 308 transmits EUV chief ray 310 to surface 312 of sample 304 at angle of illumination θ. Ray 310 reflects off of surface 312 at angle θ to TDI CCD 306, which transfers charges to generate and transmit data to processor 316 for generation of pixel images 318 of the areas of surface 312 illuminated by ray 310. In an example embodiment, angle θ is with respect to line 320 orthogonal to surface 312. Typical angles of illumination are on the order of 6 to 8 degrees.

As noted above, the use of ray 310 leads to the trigonometric coupling noted above. For example, the coupling results in apparent lateral position 218 for an imaged pixel that is displaced by amount δx (lateral error motion) from actual lateral position 216 for the pixel. When ray 310 is off-axis as illustrated in FIG. 4, vertical motions in the Z-axis are reflected as apparent lateral shift δx equal to the tangent of angle θ multiplied by vertical velocity VV of the stage. As further described below, controller 202 is arranged generate, according to angle θ, reference signal 206. In an example embodiment, controller 202 is arranged to generate signal 206 according to a trigonometric function of angle θ, for example, the tangent of angle θ.

In an example embodiment, control system 204 includes phase lock loop 222 arranged to generate control signal 224 based on reference signal 206. Control system 204 is arranged to generate pixel clock 212 using control signal 224. Loop 222 includes phase detector 226, voltage controlled oscillator (VCO) 228, divider 230, and feedback loop 232. In an example embodiment, the control system includes frequency control and phase accumulator circuit 234 arranged to modify control signal 224 according to a contour, in the Z direction, of the surface, for example, using correction branch 236, as further described below.

The following provides further detail regarding apparatus 200. As noted above, trigonometric coupling of LV and VV results in apparent position 218 for a pixel at position 216. In an example embodiment, LV and VV are measured using six-axis laser interferometer 322. These measurements are used to compute corrected lateral position 214 of an imaged pixel and to synchronize the charge transfer on TDI CCD 306 to corrected lateral position 214. Control system 204, for example, phase lock loop 222, is used to ensure synchronization of pixel clock 212 to corrected lateral position 214.

Figure 1:
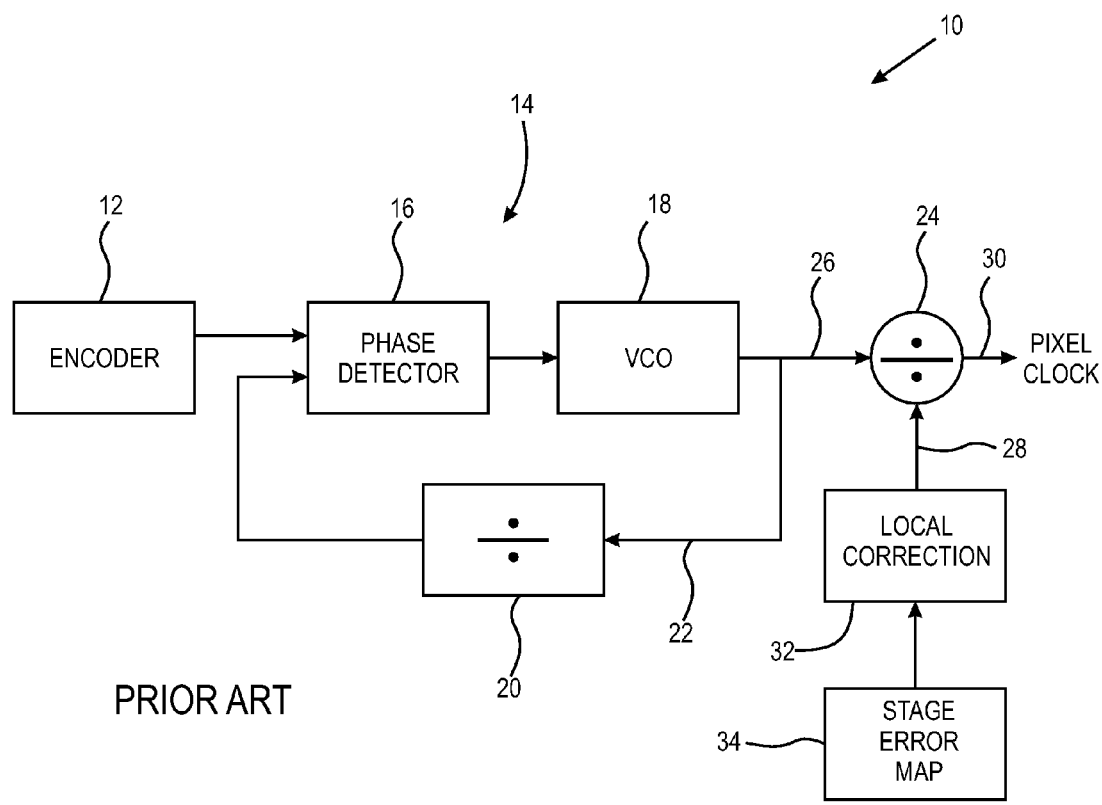
FIG. 1 is a schematic block diagram of a prior art system of generating a pixel clock for a semiconductor inspection system.
Figure 2:
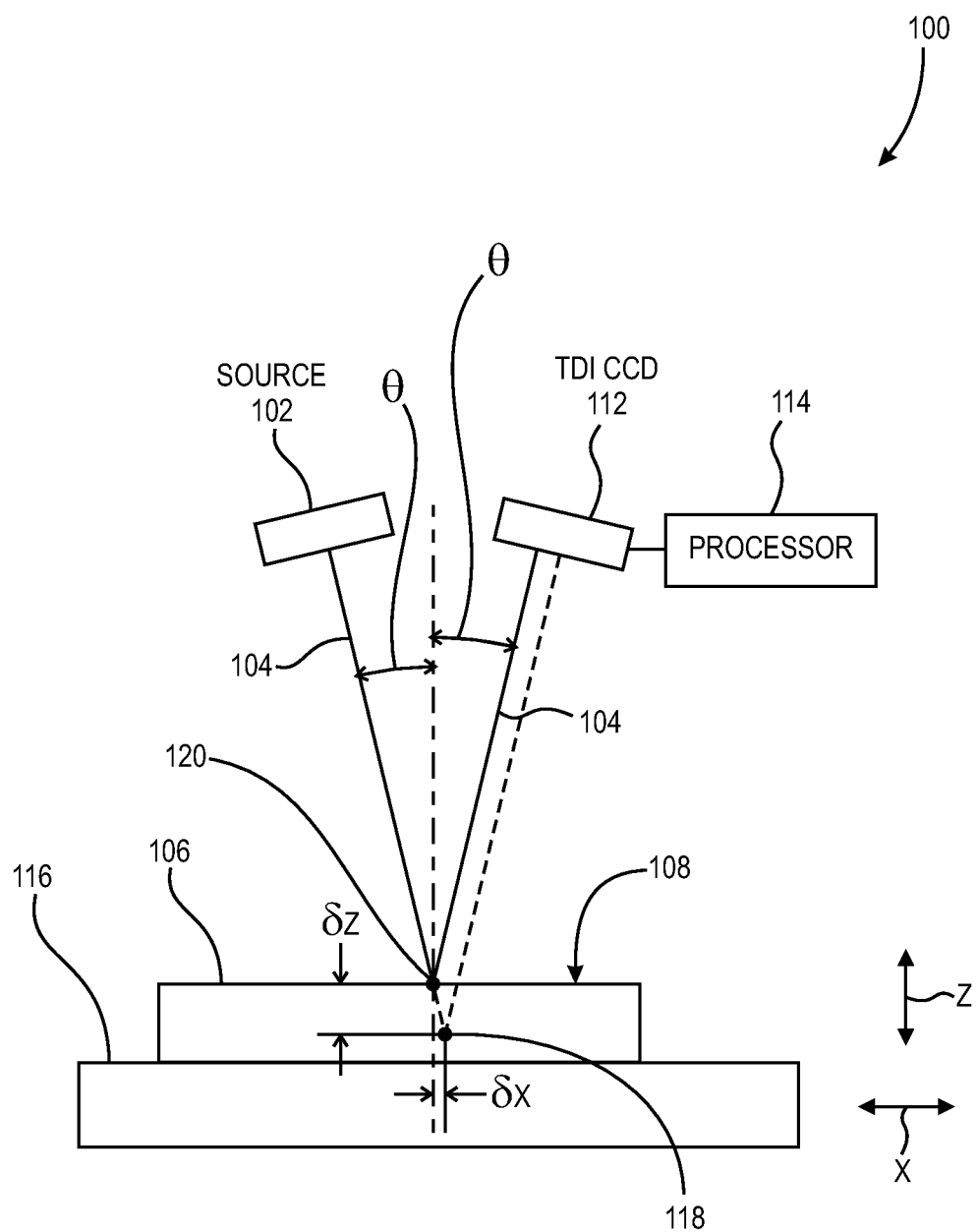
FIG. 2 is a schematic representation of a known semiconductor inspection system using off-axis illumination.

Unlike encoder 12 in FIG. 1, controller 202 generates reference signal 206 which provides compensation for the coupling of LV and VV. The additions to the firmware in the phase and frequency controller involve the coupling between the LV and VV to generate corrected position 214 of pixels being imaged. In an example embodiment, VV is multiplied by tan(θ) and combined with LV to obtain corrected position 214 and to generate signal 206. Position 214 as represented in signal 206 is used to speed up or slow down frequency output 224 of VCO 228.

As noted above, generator 202 generates phased signal 206 based LV and VV. Phase detector 266 receives signal 206 as reference input 242 and feedback loop 222 (signal 224) as input 244. As is known in the art, detector 226 compares phases for inputs 242 and 244 and outputs control signal 246 to the VCO. The VCO outputs phase and frequency signal 224 according to signal 246. As is known in the art, detector 226 modifies signal 246 as needed to bring signal 224 into phase with signal 206.

Figure 5:
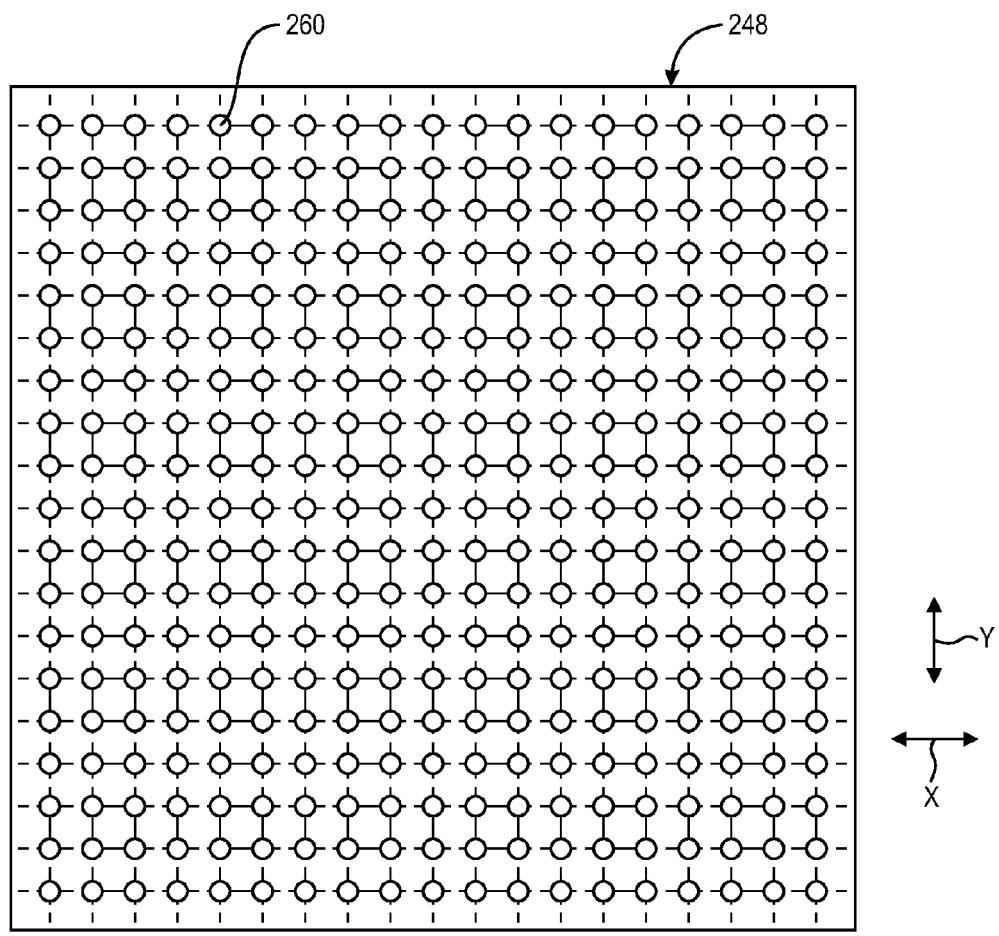
FIG. 5 is a plan view of a reticle.

FIG. 5 is a plan view of reticle 248.

Figure 6:
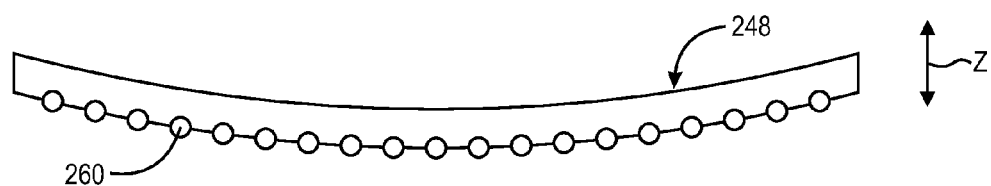
FIG. 6 is a side view of the reticle in FIG. 5.

FIG. 6 is a side view of reticle 248 in FIG. 5. Computer 250 (referred to as the IAS computer) generates X and Y coordinates, or positions, 252 and 254, respectively of a particular position on the reticle to be inspected, for example, reticle 248. X and Y coordinates 252 and 254 are generated as a function of time based on knowledge of the pattern (or lack thereof) on the reticle. X and Y coordinates 252 and 254 are used to determine the position of best focus from Z map 256 of the reticle (as a function of X and Y coordinates 252 and 254). Note that lateral velocity 210 can be derived from X and Y coordinates 252 and 254.

As shown in FIG. 6, gravity results in a "sag" of reticle 248 in the Z direction (this sag has been exaggerated in FIG. 6 for purposes of illustration). Therefore, a Z coordinate, or position, of a particular X and Y coordinate 252 and 254 cannot be assumed based on a planar X-Y surface and it is necessary to determine the actual Z position. Thus, Z map 256 is created prior to inspection and, for example, is formed by mapping the reticle surface prior to the start of the inspection of the reticle. Z coordinates 258, as a function of X and Y coordinates, are obtained from map 256. Note that vertical velocity 210 can be derived from Z coordinates 258.

As shown in FIGS. 5 and 6, reticle 248 is usually gridded and Z position 258 of the reticle (typically the surface of a multilayer for the reticle) is measured such that the patterning of the absorber does not influence the measurement. A uniform grid of points of focus drill points 260 is shown in the figures. The Z position in between focus drill points is usually interpolated using various splines. While a uniform grid is illustrated, those skilled in the art will recognize that this could just as well be applied with a non-uniform grid. Z position 258 along with X and Y positions 252 and 254 are combined to form position tuple input (reticle coordinates) 262 for the stage controller. This is usually generated over a constant sampling time interval, and velocities and accelerations are also available by computing the first and second time derivatives of these tuples. These position tuples are generated in the reticle coordinate frame, which is transformed to the stage coordinate frame by block 264. This is done through a series of both linear and (potentially) non-linear transformations, producing stage coordinates 266.

Stage map 268 in block 264 can be created by using a "golden reticle" with known feature locations and measuring stage positions corresponding to known locations of reticle 248. This information can be used to compute a series of transformation matrices. Additionally, one can map out mirrors used in metrology of the stage and use software corrections 270 to compensate for known errors and misalignments in the integration of the system. Local corrections 272 are implemented as is known in the art to generate input 274 for circuit 234.

Advantageously, apparatus 200 provides a means of automatically, accurately, and dynamically correcting lateral position distortion for a pixel on a surface of a sample being inspected by a semiconductor inspection system and synchronizing sample stage motion with a time delay integration charge-couple device in the semiconductor inspection tool.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for synchronizing sample stage motion with a time delay integration (TDI) charge-couple device (CCD) in a semiconductor inspection tool, comprising:
measuring a lateral position of a stage holding a sample being inspected;
measuring a vertical position of the stage;
determining a corrected lateral position of an imaged pixel of the sample based on the measured lateral and vertical positions; and
synchronizing, using the corrected lateral position of the imaged pixel, charge transfer of the CCD.

2. The method of claim 1, further comprising:
measuring a lateral velocity of the stage;
measuring a vertical velocity of the stage; and,
modifying the vertical velocity, wherein determining a corrected lateral position includes using the modified vertical velocity.

3. The method of claim 1, further comprising:
measuring a lateral velocity of the stage; and,
measuring a vertical velocity of the stage, wherein:
the lateral and vertical velocities are coupled;
the coupling distorts an actual lateral position of the imaged pixel; and,
determining the corrected lateral position includes compensating for the distortion.

4. The method of claim 3, wherein:
light used to charge the CCD is reflected from a surface of the sample at an acute angle;
the reference signal generator is arranged generate, according to the acute angle, a reference signal; and,
synchronizing the charge transfer includes using the reference signal to correct a difference between an apparent lateral position of the imaged pixel and the actual lateral position.

5. The method of claim 4, wherein:
the acute angle is with respect to a line orthogonal to the surface; and,
generating the reference signal includes generating the reference signal using a trigonometric function of the acute angle.

6. The method of claim 4, further comprising:
inputting the reference signal to a phase lock loop;
generating, using the phase lock loop, a control signal;
generating, using the control signal, a pixel clock; and,
synchronizing, using the pixel clock, the charge transfer.

7. The method of claim 4, further comprising:
inputting the reference signal to a phase lock loop;
generating, using the phase lock loop, a control signal;
generating a pixel clock by modifying the control signal according to a contour, in the vertical direction, of the sample; and
synchronizing, using the pixel clock, the charge transfer.

8. The method of claim 1, wherein synchronizing charge transfer includes using a phase lock loop.

9. The method of claim 1, wherein the sample is a reticle or a wafer.

10. The method of claim 1, wherein measuring the lateral and vertical positions includes using a six-axis laser interferometer.

11. The method of claim 1, further comprising:
generating a pixel clock in a phase accumulator circuit using respective corrections from stage mirrors, at least one sample height map, and at least one sample surface map; and,
synchronizing, using the pixel clock, the charge transfer.

12. An apparatus for controlling charge transfer for a time delay integration (TDI) charge-coupled device (CCD) for a semiconductor inspection system, comprising:
a phase and frequency controller arranged to generate a reference signal based on measured vertical and lateral positions of a stage holding a sample being inspected; and,
a control system arranged to generate, using the reference signal, a pixel clock to control charge transfer of the CCD for an imaged pixel of the sample in a corrected lateral position.

13. The apparatus of claim 12, wherein generating the reference signal includes modifying a vertical velocity of the stage.

14. The apparatus of claim 12, wherein:
lateral and vertical velocities of the stage are coupled;
the coupling distorts an actual lateral position of the imaged pixel; and,
generating the pixel clock includes compensating for the distortion.

15. The apparatus of claim 12, wherein:
light used to charge the CCD is reflected from a surface of the sample at an acute angle; and, the reference signal generator is arranged generate, according to the acute angle, the reference signal.

16. The apparatus of claim 12, wherein:
the control system includes a phase lock loop;
the phase lock loop is arranged to generate a control signal based on the reference signal; and
the control system is arranged to generate the pixel clock using the control signal.

17. The apparatus of claim 16, wherein the control system is arranged to modify the control signal according to a contour, in the z direction, of the surface.

18. An apparatus for controlling charge transfer for a time delay integration (TDI) charge-coupled device (CCD) for a semiconductor inspection system, comprising:
a phase and frequency controller arranged to generate a reference signal based on measured vertical and lateral positions of a stage holding a sample being inspected; and,
a control system:
including a phase lock loop arranged to generate a control signal based on the reference signal; and,
arranged to generate, using the control signal, a pixel clock to control charge transfer of the CCD and to correct a difference between an apparent lateral position of an imaged pixel of the sample and an actual lateral position of the imaged pixel, wherein:
light used to charge the CCD is reflected from a surface of the sample at an acute angle; and,
the reference signal generator is arranged to generate the reference signal based on the acute angle.

19. The apparatus of claim 18, wherein the control system is arranged to modify the control signal, according to a contour of the surface in the vertical direction, to generate the pixel clock.

* * * * *